(12) United States Patent
Park et al.

(10) Patent No.: US 6,436,921 B1
(45) Date of Patent: Aug. 20, 2002

(54) CARBAPENEM DERIVATIVES AND A PREPARATION METHOD THEREOF

(75) Inventors: Sang Woo Park; Dong Kin Kim; Kye-Jung Shin; Yong Koo Kang, all of Seoul; Yong Zu Kim, Daejon; Yong Ho Chung; Hong Woo Lee, both of Kyungki-Do; Jae Doo Huh, Seoul; Sang Joo Lee, Kyunki-Do; Il Hong Suh; Bong Suk Ko, both of Kyungki-Do, all of (KR)

(73) Assignees: Korea Institute of Science and Technology, Seoul; Il Hwa Co., Ltd., Kyungki-Do, both of (KR)

( * ) Notice: Subject to any disclaimer, the term of this patent is extended or adjusted under 35 U.S.C. 154(b) by 0 days.

(21) Appl. No.: 09/508,656

(22) PCT Filed: Aug. 21, 1998

(86) PCT No.: PCT/KR98/00255

§ 371 (c)(1),
(2), (4) Date: May 18, 2000

(87) PCT Pub. No.: WO99/14218

PCT Pub. Date: Mar. 25, 1999

(30) Foreign Application Priority Data

Sep. 13, 1997 (KR) .......................................... 97-47460

(51) Int. Cl.$^7$ .................... C07D 477/20; A61K 31/407; A61K 31/454; A61K 31/5377; A61P 31/04

(52) U.S. Cl. .................. 514/210.13; 540/350; 548/536; 548/537

(58) Field of Search ...................... 540/350; 514/210.13

(56) References Cited

U.S. PATENT DOCUMENTS 4,933,333 A * 6/1990 Sunagawa .................... 540/310

FOREIGN PATENT DOCUMENTS

EP 0 443 883 8/1991

* cited by examiner

Primary Examiner—Mark L. Berch
(74) Attorney, Agent, or Firm—Darby & Darby

(57) ABSTRACT

The present invention relates to carbapenem derivatives of Formula I, wherein X is carbonyl or sulfonyl, and a preparation method thereof. The carbapenem derivatives of the invention have excellent antibacterial properties and are thus useful as antibiotics.

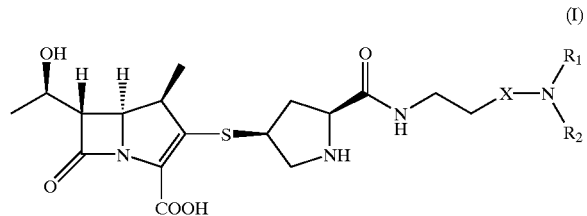

(I)

16 Claims, 1 Drawing Sheet

CARBAPENEM DERIVATIVES AND A PREPARATION METHOD THEREOF

TECHNICAL FIELD

The present invention relates to carbapenem derivatives of the following formula (I) and a preparation method thereof. The carbapenem derivatives can be used as antibiotics since they have excellent antibacterial activities.

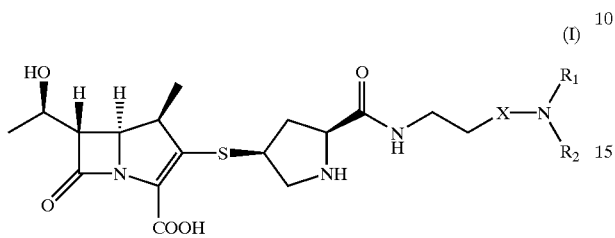

(I)

wherein X is carbonyl or sulfonyl group, $R_1$ and $R_2$ are hydrogen, low alkyl or aliphatic cyclic alkyl groups and when $R_1$ is hydrogen, $R_2$ is hydrogen, methyl, hydroxyethyl or allyl group and when $R_1$ is methyl $R_2$ is methyl, hydroxyethyl or allyl group; or $R_1$ and $R_2$ taken together with a nitrogen atom to which they are attached, is a heterocyclic group such as pyrrolidinyl, morpholinyl and piperidinyl group.

BACKGROUND OF THE INVENTION

The commercially available carbapenem antibiotics so far include thienamycin and imipenem as described in the literature (*J. Antibiot.*, 1979, 32, 1). However, these compounds can be degraded by human renal enzyme (renal dehydropeptidase I, DHP-I) and lose their activity.

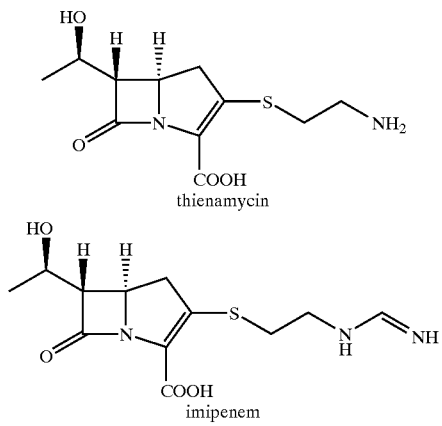

thienamycin imipenem

DISCLOSURE OF THE INVENTION

Figure 1:
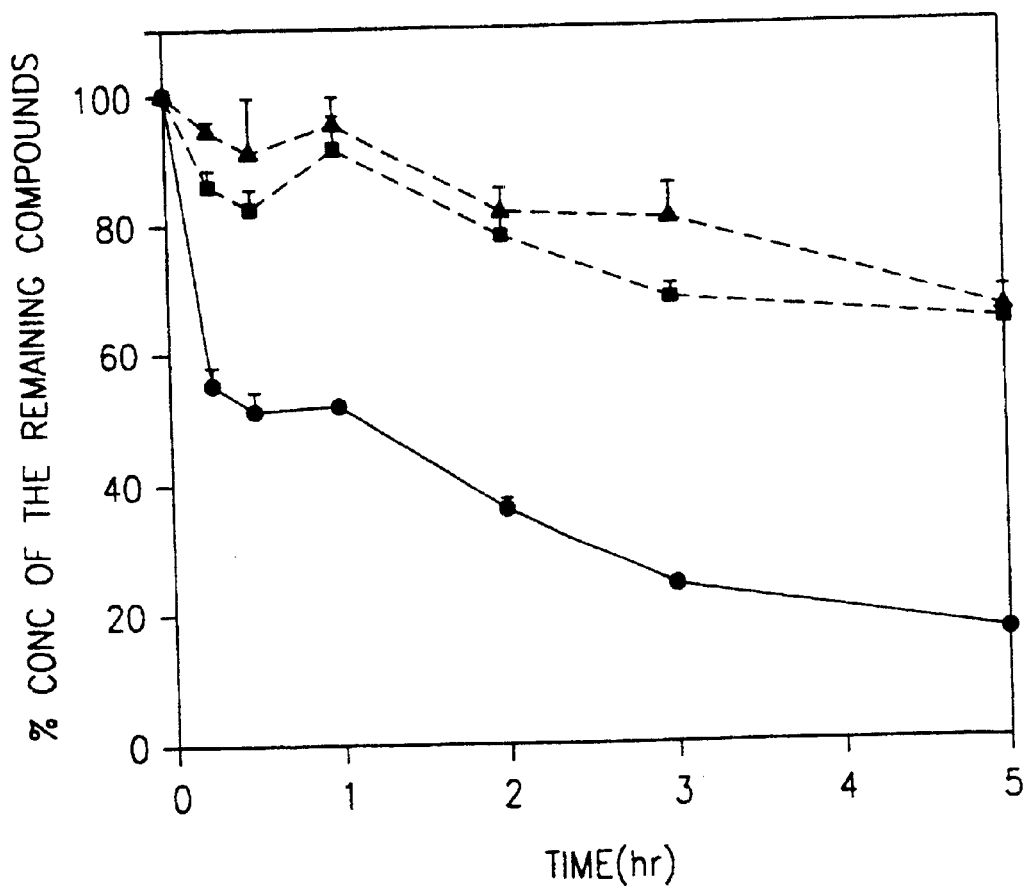
FIG. 1 is a graph showing the stability of the compounds of the present invention and the prior art compound meropenem, against the attack of a rela enzyme (DHP-1).

In developing the carbapenem derivatives that are stable to the attack of DHP-I and have high bactericidal property, the present inventors have synthesized the carbapenem derivatives that have excellent characteristics.

Briefly, the preparation method of the carbapenem derivatives represented by the formula I comprises first preparing the carbapenem intermediate represented by the formula VII by reacting the carbapenem, the parent cyclic compound represented by formula II with diphenylchlorophosphate or trifluoromethansulfonic anhydride in the presence of base. Then the carbapenem intermediate represented by the formula VII is reacted with thiol derivatives represented by the formula III to produce the carbapenem derivatives represented by the formula I.

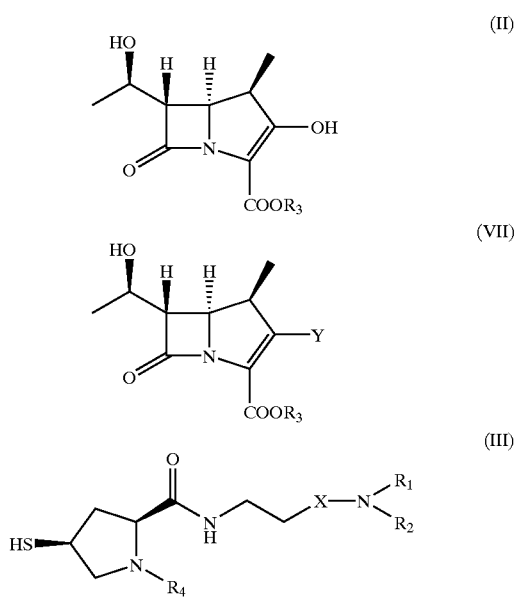

In the formula II, $R_3$ represents p-nitrobenzyl or allyl group. In the formula III, $R_4$ represents p-nitrobenzyloxycarbonyl or allyloxycarbonyl group, X is carboxylic or sulfonyl group. $R_1$ and $R_2$ are hydrogen, lower alkyl or aliphatic cyclic alkyl groups. When $R_1$ is hydrogen, $R_2$ is hydrogen, methyl, hydroxyethyl or allyl group and when $R_1$ is methyl $R_2$ is methyl, hydroxyethyl or allyl group; or $R_1$ and $R_2$ are taken together with a nitrogen atom to which they are attached, is a heterocyclic group such as pyrrolidinyl, morpholinyl and piperidinyl group. In the formula VII, R is a protecting group such as p-nitrobenzyl or allyl group. Y in the formula VII represents —OPO(OPh)$_2$ or —OSO$_2$CF$_3$.

Before describing the preparation method of the present invention, we will first describe the reactants that are used in the present invention in detail.

First, the thiol derivative, which is one of the reactants, represented by the formula III is obtained by reacting the acid compound represented by the formula IV and the amine derivative represented by the formula V via amide formation reaction.

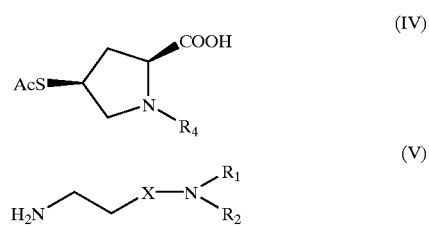

In the formula IV, $R_4$ is a protecting group and is p-nitrobenzyloxylcarbonyl or allyloxycarbonyl group. In the formula V, X is carbonyl or sulfonyl group. $R_1$ and $R_2$ are hydrogen, lower alkyl or aliphatic cyclic alkyl groups. When $R_1$ is hydrogen, $R_2$ is hydrogen, methyl, hydroxyethyl or allyl group and when $R_1$ is methyl $R_2$ is methyl, hydroxyethyl or allyl group; or $R_1$ and $R_2$ are taken together with a nitrogen atom to which they are attached, is a heterocyclic group such as pyrrolidinyl, morpholinyl and piperidinyl group.

(1). Before preparing the thiol derivative represented by the formula III, the amide represented by the formula VI is prepared by the reaction of acid compound of the formula IV with amine of the formula V and ethyl chloroformate in the presence of bases such as tertiary ethylamine and tertiary methylamine in tetrahydrofuran as a solvent at −5~5° C., preferably at 0° C. for an hour.

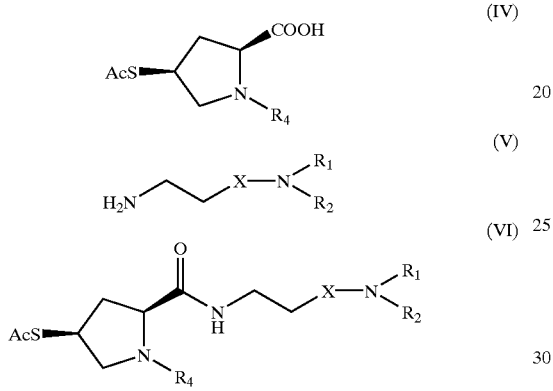

In the formula VI, $R_4$ is a protecting group such as p-nitrobenzyloxylcarbonyl or allyloxycarbonyl group. In the formula V, X is carbonyl or sulfonyl group. $R_1$ and $R_2$ are hydrogen, lower alkyl or aliphatic cyclic alkyl groups. When $R_1$ is hydrogen, $R_2$ is hydrogen, methyl, hydroxyethyl or allyl group and when $R_1$ is methyl $R_2$ is methyl, hydroxyethyl or allyl group; or, $R_1$ and $R_2$ are taken together with a nitrogen atom to which they are attached, is a heterocyclic group such as pyrrolidinyl, morpholinyl and piperidinyl group.

(2). The amide represented by the formula VI according to (1) is reacted with an aqueous solution of 2N sodium hydroxide in methanol, ethanol or isopropanol as a solvent at −5~5° C., preferably at 0° C. for 10~30 minutes to produce the thiol derivatives represented by the formula III.

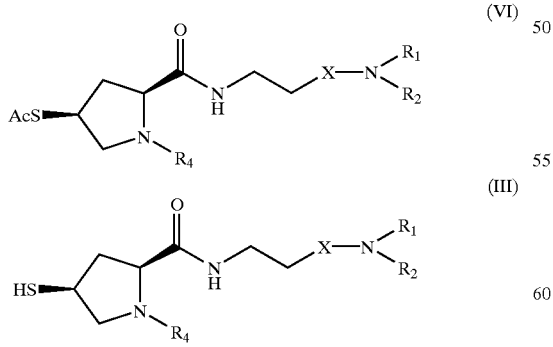

The amine derivatives represented by the formula V can be prepared easily by using β-alanine or taurine as a reactant in case X is carbonyl or sulfonyl, respectively (*J. Am. Chem. Soc.*, 1947, 69, 1393).

Above, we describe in detail the preparation method of the reactants for the preparation of he carbapenem derivatives represented by the formula I. The carbapenem derivatives of the formula I can be prepared by using the following three procedures as described below in detail.

(1). The first procedure that the parent cyclic compound, carbapenem as represented by the formula II is reacted with diphenylchlorophosphate or trifluoromethansulfonic anhydride in the presence of a base, diisopropylethylamine in acetonitril as a solvent at −5~5° C., preferably at 0° C. for an hour to obtain the carbapenem intermediate represented by the formula VII.

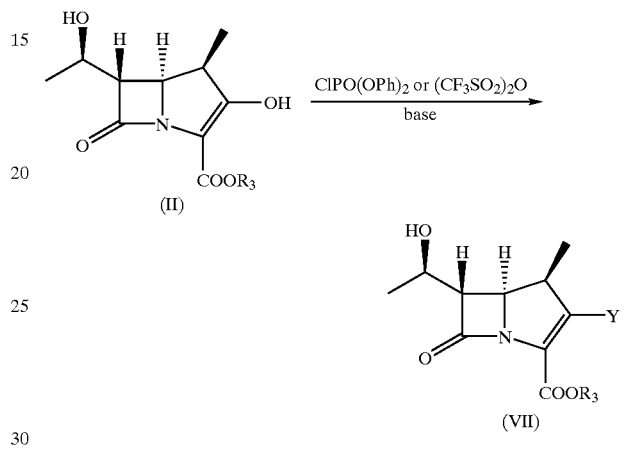

In the formulas II and VII, $R_3$ is a protecting group and is p-nitrobenzyl or allyl. Y in the formula VII is —OPO(OPh)$_2$ or —OSO$_2$CF$_3$.

(2). The second procedure that the carbapenem intermediate represented by the formula VII is reacted with the thiol derivative represented by the formula III in the presence of a base, diisopropylethylamine in acetonitril as a solvent at −5~5° C., preferably at 0° C. for 5~24 hours to obtain the carbapenem derivative that is protected by R (hereinafter will be called "protected carbapenem derivative") represented by the formula VIII.

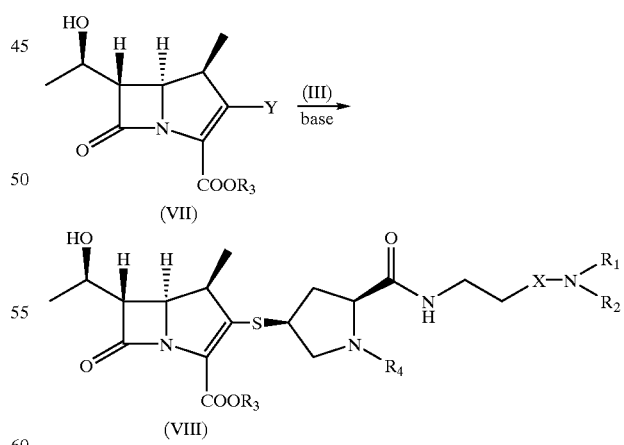

In the formula VIII, X represents carbonyl or sulfonyl group. $R_1$ and $R_2$ are hydrogen, lower alkyl or aliphatic cyclic alkyl groups. When $R_1$ is hydrogen, $R_2$ is hydrogen, methyl, hydroxyethyl or allyl group and when $R_1$ is methyl, $R_2$ is methyl, hydroxyethyl or allyl group; or, $R_1$ and $R_2$ are taken together with a nitrogen atom to which they are attached, is a heterocyclic group such as pyrrolidinyl, morpholinyl and piperidinyl group.

(3) The third procedure that the protected carbapenem derivative represented by the formula VIII is reacted with hydrogen gas (1~3 atm, preferably 2 atm) in the presence of palladium/carbon as catalysts in a 1:1 mixture of tetrahydrofuran/water as the reaction solvent at 15~30° C., preferably at 20° C. for 3 hours to remove the protecting group and produce the carbapenem derivative Iu of the formula I.

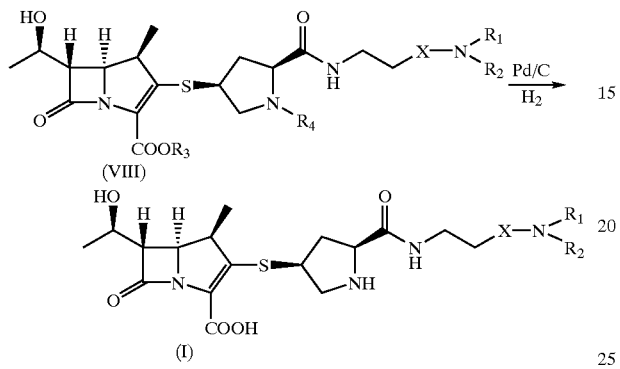

The carbapenem derivative represented by the formula I showed excellent results in the minimum inhibitory concentration test (MIC test) against the gram-negative and gram-positive bacteria and were stable against the enzymatic attack of DHP-1. Moreover, the carbapenem derivative represented by the formula I had higher bioavailbility than the conventional antibiotics.

Method for Carrying Out the Invention

The invention will be further illustrated by the following examples, but not limited to the examples given.

EXAMPLE 1

N-(t-Butyloxycarbonyl)-β-alanine

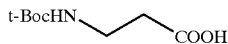

Beta-alanine, 17.8 g (0.2 mol) and 22 g of triethylamine (0.22 mol) were mixed and stirred in 150 ml of dichloromethane at 0° C. Di-t-butyldicarbonate, 43.5 9 g (0.2 mol) dissolved in 50 ml of dichloromethane was slowly added to above solution. The reaction mixture was stirred for an hour at 0° C. and subsequently extracted with dichloromethane and 100 ml of cold 1 N hydrochloric acid aqueous solution. The extracted dichloromethane solution was dried to obtain 36 g (95%) of N-(t-butyloxycarbonyl)-β-alanine.

NMR (CDCl$_3$) δ: 1.43 (s, 9H), 2.56 (bs, 2H), 3.38 (bs, 2H), 5.11 (bs, 1H), 10.61 (bs, 1H)

EXAMPLE 2

N-(t-Butyloxycarbonyl)-β-alanine Dimethylamide

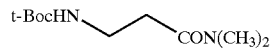

N-(t-Butyloxycarbonyl)-β-alanine, 3.8 g (20 mmol) was dissolved in 50 ml of tetrahydrofuran, and the solution was cooled to 0° C. and stirred. To this mixture, 2.4 g (24 mmol) of triethylamine was added and 2.16 g (20 mmol) of ethyl chloroformate was slowly added. After stirring the reaction mixture for an hour at 0° C., 4 ml of 40% diethylamine aqueous solution was slowly added and stirred vigorously for an hour. The mixture was extracted by adding 100 ml of dichloromethane and 50 ml of water. The organic layer was washed with 1 N HCl aqueous solution and subsequently with saturated sodium bicarbonate aqueous solution. The washed mixture was dried to obtain 3.9 g (90%) of N-(t-butyloxy-carbonyl)-β-alanine dimethylamide.

NMR (CDCl$_3$) δ: 1.42 (s, 3H), 2.49 (t, 2H), 2.94 (s, 3H), 2.97 (s, 3H), 3.40 (q, 2H), 5.37 (bs, 1H)

EXAMPLE 3

Trifluoroacetic Acid Salf of β-alanine Dimethylamide Trifluoroacetate

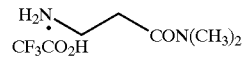

N-(t-Butyloxycarbonyl)-β-alanine dimethylamide, 3.5 g (16.2 mmol) was dissolved in 10 ml of dichloromethane, and 50 ml of trifluoroacetic acid was added. After stirring the reaction mixture for 2 hours at room temperature, the solution including an excess amount of trifluoroacetic acid was distilled at reduced pressure to obtain 3.7 g (99%) of trifluoroacetic acid salt of β-alanine dimethylamide.

NMR (D$_2$O) δ: 1.18 (d, 3H), 1.26 (d, 3H)

EXAMPLE 4

N-phthalimido Taurine

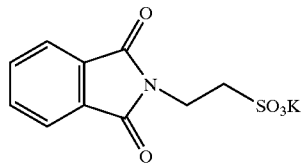

Taurine, 62.6 g (0.5 mol) and 52.5 g (0.535 mol) of potassium acetate were mixed in 175 ml of acetic acid and refluxed for 10 minutes. Phthalic anhydride, 79.2 g (0.535 mol) was added into this mixture and stirred for 2 hours. White precipitate was produced when the mixture was cooled to 0° C. and stirred. The crystals were filtered at reduced pressure, washed with acetic acid and ethanol and dried to obtain 105 g (71%) of the potassium salt of N-phthalimidotaurine.

NMR (D$_2$O) δ: 3.26 (t, 2H), 4.02 (t, 2H), 7.71~7.79 (m, 4H)

EXAMPLE 5

N-Phthalimidotaurine Dimethylamide

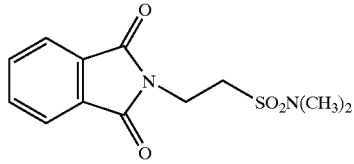

Potassium salt of N-phthalimidotaurine, 4.4 g (15 mmol) and 4.5 g (22 mmol) phosphorous pentachloride were mixed in 22 ml of anhydrous benzene and refluxed under heat for 3 hours. The reactant was dispersed in ice cold water to obtain a white precipitate. The crystal was filtered under reduced pressure and dried. The crystal was dissolved in 50 ml of tetrahydrofuran, and subsequently 4 ml of 40% dimethylamine aqueous solution was added slowly. The reaction mixture was stirred for an hour at room temperatures and distilled under reduced pressure to obtain the crystal. The product was recrystallized to obtain 3.7 g (87%) of N-phthalimidotaurine dimethylamide.

NMR (DMSO-$d_6$) δ: 2.77 (s, 6H), 3.40 (t, 2H), 3.96 (t, 2H), 7.82–7.88 (m, 4H)

EXAMPLE 6

Taurine Dimethylamide Hydrochloride

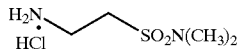

After dissolving 3.5 g (12.4 mmol) of N-phthalimidotaurine dimethylamide in 40 ml of 95% ethanol, the mixture was refluxed under heat for 3 hours with 0.62 g (12.4 mmol) of hydrazine hydrate. The reaction mixture was distilled under reduced pressure to remove the solvent. 100 mL of water was added and the pH was adjusted to 3 by adding dilute hydrochloric acid. After removing water completely by distillation under reduced pressure, the product was recrystallized with chloroform to obtain 2.2 g (94%) of taurine dimethylamide hydrochloride.

NMR ($D_2O$) δ: 2.77 (t, 2H), 3.05 (s, 3H), 3.24 (s, 3H), 3.60 (t, 2H)

EXAMPLE 7

(2S,4S)-N-(4-Nitrobenzyloxycarbonyl)-2-dimethylamidoethyl-carbamoyl-4-acetylthiopyrrolidine

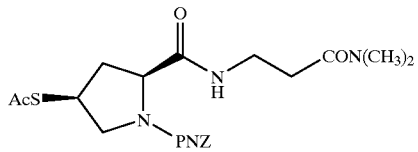

(2S,4S)-N-(4-Nitrobenzyloxycarbonyl)-2-carboxy-4-acetylthio pyrrolidine, 3.68 g (10 mmol) was dissolved in 50 ml of tetrahydrofuran, cooled to 0° C., and stirred. To this solution, 1.2 g (12 mmol) of triethylamine was added and 1.08 g (10 mmol) of ethyl chloroformate was slowly added. After stirring the mixture for an hour at 0° C., 2.3 g (10 mmol) of trifluoroacetic acid salt of β-analine dimethylamide was slowly added and stirred vigorously for an hour. After an extraction with 100 ml dichloromethane and 50 ml of water, the organic layer was washed with 1 N HCl aqueous solution and then with saturated sodium bicarbonate solution and dried by evaporating the solvent. Purification was done by using column chromatography to obtain 3.2 g (69%) of (2S,4S)-N-(4-nitrobenzyloxycarbonyl)-2-dimethylamidoethylcarbamoyl-4-acetylthiopyrrolidine.

NMR (CDCl$_3$) δ: 2.32 (s, 2H), 2.93 (s, 3H), 2.97 (s, 3H), 3.41 (dd, 1H), 3.56 (bs, 2H), 5.23 (m, 2H), 7.08 (bs, 1H), 7.52 (d, 2H), 8.22 (d, 2H)

EXAMPLE 8

(2S,4S)-N-(4-nitrobenzyloxycarbonyl)-2-dimethylsulfoneamidoethyl-carbamoyl-4-acetylthio Pyrrolidine

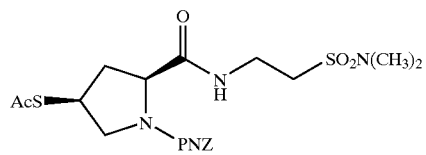

(2S,4S)-N-(4-Nitrobenzyloxycarbonyl)-2-carboxy-4-acetylthiopyrrolidine, 3.68 g (10 mmol) was dissolved in 50 ml of tetrahydrofuran, cooled to 0° C., and stirred. To this solution, 1.2 g (12 mmol) of triethylamine was added and 1.08 g (10 mmol) of ethyl chloroformate was slowly added. After stirring the mixture for an hour at 0° C., 1.9 g (10 mmol) of taurine dimethylamide hydrochloride was slowly added and stirred vigorously for an hour. After an extraction with 100 ml dichloromethane and 50 ml of water, the organic layer was washed with 1 N HCl aqueous solution and then with saturated sodium bicarbonate solution and dried by evaporating the solvent. Purification was done by using column chromatography to obtain 3.3 g (64%) of (2S,4S)-N-(4-nitrobenzyloxycarbonyl)-2-dimethylsulfoneamidoethyl-carbamoyl-4-acetylthiopyrrolidine.

NMR (CDCl$_3$) δ: 2.29 (s, 3H), 2.84 (s, 6H), 3.08 (m, 2H), 3.69 (m, 2H), 5.21 (bs, 2H), 7.17 (bs, 1H), 7.49 (d, 2H), 8.17 (d, 2H)

EXAMPLE 9

(2S,4S)-N-(4-Nitrobenzyloxycarbonyl)-2-dimethylamidoethyl-carbamoyl-4-mercaptopyrrolidine

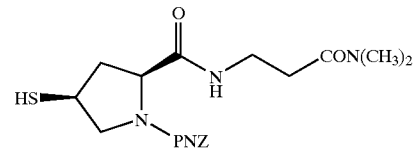

(2S,4S)-N-(4-Nitrobenzyloxycarbonyl)-2-dimethylamidoethylcarbamoyl-4-acetylthiopyrrolidine, 2.3 g (5 mmol) was dissolved in 50 ml of methanol, cooled to 0° C. 3 ml of 2 N sodium hydroxide aqueous solution was slowly added. After stirring the mixture for 10 minutes, dichloromethane and water were added to separate the organic layer. The organic layer was dried by evaporation. to obtain 2.0 g (86%) of (2S,4S)-N-(4-nitrobenzyloxycarbonyl)-2-dimethylamidoethyl-carbamoyl-4-mercaptopyrrolidine.

NMR (CDCl₃) δ: 2.95 (s, 3H), 2.99 (s, 3H), 3.56 (m, 2H), 5.22 (m, 2H), 7.50 (d, 2H), 8.19 (d, 2H)

EXAMPLE 10

(2S,4S)-N-(4-Nitrobenzyloxycarbonyl)-2-dimethylsulfoneamidoethylcarbamoyl-4-mercaptopyrrolidine

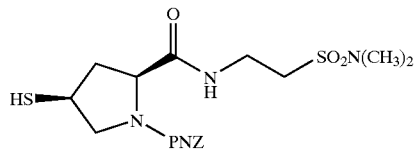

(2S,4S)-N-(4-Nitrobenzyloxycarbonyl)-2-dimethylsulfoneamidoethylcarbamoyl-4-acetylthiopyrrolidine, 2.6 g (5 mmol) was dissolved in 50 ml of methanol, cooled to 0° C. 3 ml of 2 N sodium hydroxide aqueous solution was slowly added. After stirring the mixture for 10 minutes, dichloromethane and water were added to separate the organic layer. The organic layer was dried by evaporation to obtain 2.2 g (93%) of (2S, 4S)-N-(4-nitrobenzyloxycarbonyl)-2-dimethylsulfoneamidoethylcarbamoyl-4-mercaptopyrrolidine.

NMR (CDCl₃) δ: 2.80 (s, 6H), 3.05 (m,23H), 3.65 (m, 2H), 5.20 (s, 2H), 7.47 (d, 2H), 8.16 (d, 2H)

EXAMPLE 11

(1R,5R,6S,8R,2'S,4'S)-2-[1'-(Nitrobenzyloxycarbonyl)-2'-dimethylamidoethylcarbamoylpyrrolidin-4'-ylthio]-6-(1-hydroxyethyl)-1-methylcarbapen-2-em-3-carboxylic Acid 4-nitrobenzyl Ester

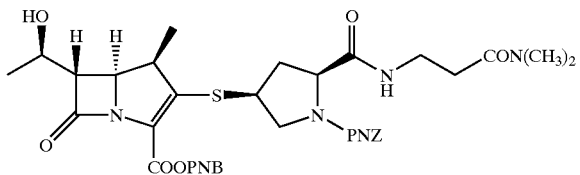

(1R,5R,6S,8R)-6-(1-Hydroxyethyl)-1-methyl-2-diphenylphosphoryloxycarbapen-2-em-3-carboxylic acid 4-nitrobenzyl ester, 1.13 g (2 mmol) was dissolved in 15 ml of acetonitrile. To this mixture, diisopropylethylamine 0.42 ml (2.4 mmol) and subsequently 848 mg (2 mmol) of (2S,4S)-N-(4-nitrobenzyloxycarbonyl)-2-dimethylamidoethylcarbamoyl-4-mercaptopyrrolidine was added at 0° C. After stirring the mixture for 24 hours, the solvent was removed by distillation under reduced pressure. The remainder was purified by column chromatography to obtain 0.9 g (60%) of (1R,5R,6S,8R,2'S,4'S)-2-[1'-(nitrobenzyloxycarbonyl)-2'-dimethylamido-ethylcarbamoylpyrrolidin-4'-ylthio]-6-(1-hydroxyethyl)-1-methylcarbapen-2-em-3-carboxylic acid 4-nitrobenzyl ester.

NMR (CDCl₃) δ: 1.25 (d, 3H), 1.34 (d, 3H), 2.90 (s, 3H), 2.98 (s, 3H), 5.14–5.50 (m, 4H), 7.08 (bs, 1H), 7.48 (d, 2H), 7.64 (d, 2H), 8.19 (d, 4H)

EXAMPLE 12

(1R,5R,6S,8R,2'S,4'S)-2-[1'-(Nitrobenzyloxycarbonyl)-2'-dimethylsulfoneamidoethylcarbamoypyrrolidin-4'-ylthio]-6-(1-hydroxyethyl)-1-methylcarbapen-2-em-3-carboxylic Acid 4-nitrobenzyl Ester

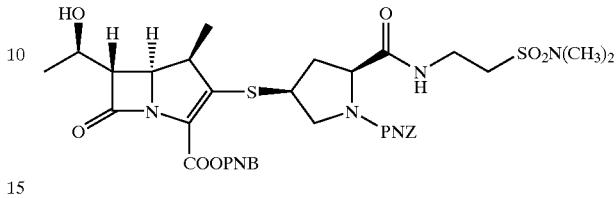

(1R,5R,6S,8R)-6-(1-Hydroxyethyl)-1-methyl-2-diphenylphosphoryloxycarbapen-2-em-3-carboxylic acid 4-nitrobenzyl ester, 1.13 g (2 mmol) was dissolved in 15 ml of acetonitrile. To this mixture, diisopropylethylamine 0.42 ml (2.4 mmol) and subsequently 944 mg (2 mmol) of (2S,4S)-N-(4-nitrobenzyloxycarbonyl)-2-domethylsulfoneamidoethylcarbamoyl-4-mercaptopyrrolidine was added at 0° C. After stirring the mixture for 24 hours, the solvent was removed by distillation under reduced pressure. The remainder was purified by column chromatography to obtain 1.1 g (70%) of (1R,5R,6S,8R,2'S,4'S)-2-[1'-(Nitrobenzyloxycarbonyl)-2'-dimethylsulfoneamidoethylcarbamoypyrrolidin-4'-ylthio]-6-(1-hydroxyethyl)-1-methylcarbapen-2-em-3-carboxylic acid 4-nitrobenzyl ester.

NMR (CDCl₃) δ: 1.27 (d, 3H), 1.36 (d, 3H), 2.86 (s, 6H), 3.13 (m, 2H), 3.74 (m, 2H), 5.22 (d, 1H), 5.25 (s, 2H), 5.50 (d, 1H), 7.12 (bs, 1H), 7.51 (d, 2H), 7.66 (d, 2H), 8.22 (d, 4H)

EXAMPLE 13

(1R,5R,6S,8R,2'S,4'S)-2-[2'-Dimethylamidoethylcarbamoylpyrrolidin-4'-ylthio]-6-(1-hydroxyethyl)-1-methylcarbapen-2-em-3-carboxylic Acid

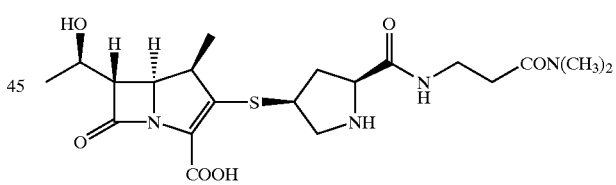

(1R,5R,6S,8R,2'S,4'S)-2-[1'-(Nitrobenzyloxycarbonyl)-2'-dimethylamidoethylcarbamoylpyrrolidin-4'-ylthio]-6-(1-hydroxyethyl)-1-methylcarbapen-2-em-3-carboxylic acid 4-nitrobenzyl ester, 0.8 g (1.06 mmol) was dissolved in 10 ml of tetrahydrofuran and 10 ml of water. 500 mg of 10% palladium/carbon was added to this mixture. The reaction mixture underwent the hydrogenation reaction under 2 atm hydrogen for 3 hours. The mixture was filtered and distilled under reduced pressure at 5–10° C. The remainder was purified by column chromatography using the Diaion ion exchange resin and freeze-dried to obtain 270 mg (56%) of (1R,5R,6S,8R,2'S,4'S)-2-[2'-dimethylamidoethylcarbamoylpyrrolidin-4'-ylthio]-6-(1-hydroxyethyl)-1-methylcarbapen-2-em-3-carboxylic acid.

NMR (D₂O) δ: 1.18 (d, 3H), 1.26 (d, 3H), 2.01 (m, 1H), 2.67 (m, 2H), 2.90 (s, 3H), 3.04 (s, 3H), 3.32–3.56 (m, 6H), 3.76 (dd, 1H), 4.00 (dq, 1H), 4.21 (t, 1H), 4.41 (t, 1H)

EXAMPLE 14

(1R,5R,6S,8R,2'S,4'S)-2-[2'-Dimethylsulfoneamidoethylcarbamoylpyrrolidin-4'-ylthio]-6-(1-hydroxyethyl)-1-methylcarbapen-2-em-3-carboxylic Acid

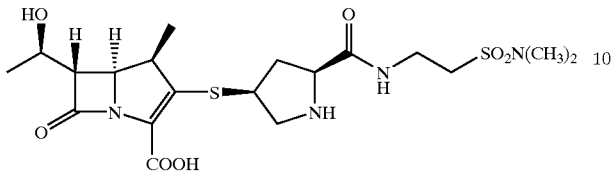

(1R,5R,6S,8R,2'S,4'S)-2-[1'-(Nitrobenzyloxycarbonyl)-2'-dimethylsulfoneamidoethylcarbamoylpyrrolidin-4'-ylthio]-6-(1-hydroxyethyl)-1-methylcarbapen-2-em-3-carboxylic acid 4-nitrobenzylester, 1.0 g (1.26 mmol) was dissolved in 10 ml of tetrahydrofuran and 10 ml of water. 500 mg of 10% palladium/carbon was added to this mixture. The reaction mixture underwent the hydrogenation reaction under 2 atm hydrogen for 3 hours. The mixture was filtered and distilled under reduced pressure at 5–10° C. The remainder was purified by column chromatography using the Diaion exchange resin and freeze-dried to obtain 320 mg (52%) of (1R,5R,6S,8R,2'S,4'S)-2-[2'-dimethylsulfoneamidoethylcarbamoylpyrrolidin-4'-ylthio]-6-(1-hydroxyethyl)-1-methylcarbapen-2-em-3-carboxylic acid.

NMR (D$_2$O) δ: 1.22 (d, 3H), 1.30 (d, 3H), 2.11 (m, 1H), 2.89 (s, 6H), 2.93 (m, 1H), 3.34–3.49 (m, 5H), 3.65–3.87 (m, 4H), 4.05 (dq, 1H), 4.26 (t, 1H), 4.48 (t, 1H)

EXAMPLE 15

The carbapenem derivative, (1R,5R,6S,8R)-6-(1-hydroxyethyl)-1-methyl-2-diphenylphosphoryloxycarbapen-2-em-3-carboxylic acid 4-nitrobenzyl ester, represented by the formula VII and various β-alanine and taurine derivatives represented by the formula III were reacted to obtain the compounds in Tables 1 and 2 according to the procedures as in Examples 11, 12, 13 and 14.

TABLE 1

| Compound No. | R |
|---|---|
| 1 | NH$_2$ |
| 2 | NHCH$_3$ |
| 3 | NHCH$_2$CH$_2$OH |
| 4 | N(CH$_2$)$_4$ |
| 5 | N(CH$_2$)$_4$O |
| 6 | N(CH$_3$)CH$_2$CH$_2$OH |
| 7 | NHCH$_2$CH=CH$_2$ |
| 8 | N(CH$_2$)$_5$ |
| 9 | N(CH$_3$)CH$_2$CH=CH$_2$ |

TABLE 2

| Compound No. | R |
|---|---|
| 10 | NH$_2$ |
| 11 | NHCH$_3$ |
| 12 | NHCH$_2$CH=CH$_2$ |
| 13 | NHCH$_2$CH$_2$OH |
| 14 | N(CH$_3$)CH$_2$CH$_2$OH |
| 15 | N(CH$_2$)$_4$ |
| 16 | N(CH$_2$)$_4$O |
| 17 | N(CH$_2$)$_5$ |
| 18 | N(CH$_3$)CH$_2$CH=CH$_2$ |

The NMR data for the compounds of Tables 1 and 2 are as follows:

Compound 1: (D$_2$O) δ: 1.24 (d, 3H, J=7.2 Hz, β-methyl), 1.33 (d, 3H, J=6.4 Hz, CH$_3$CHOH), 2.06–2.11 (m, 1H), 2.56–2.60 (m, 2H), 2.94, 2.99 (m, 1H), 3.37–3.65 (m, 5H), 3.76–3.82 (m, 1H), 4.04, 4.08 (m, 1H), 4.25–4.31 (m, 2H), 4.50 (t, 1H).

Compound 2: (D$_2$O) δ: 1.22 (d, 3H, J=7.1 Hz, β-methyl), 1.33 (d, 3H, J=6.3 Hz, CH$_3$CHOH), 2.06–2.13 (m, 1H), 2.54–2.68 (m, 2H), 2.77 (s, 3H), 2.78, 3.02 (m, 1H), 3.37–3.65 (m, 5H), 3.75–3.83 (m, 1H), 3.98, 4.08 (m, 1H), 4.24–4.31 (m, 2H), 4.46 (t, 1H).

Compound 3: (D$_2$O) δ: 1.22 (d, 3H, J=7.1 Hz, β-methyl), 1.31 (d, 3H, J=6.4 Hz, CH$_3$CHOH), 2.04–2.09 (m, 1H), 2.54–2.59 (m, 2H), 2.94–2.99 (m, 1H), 3.36–3.65 (m, 7H), 3.76, 3.85 (m, 3H), 4.02, 4.06 (m, 1H), 4.24–4.30 (m, 2H), 4.47 (t, 1H).

Compound 4: (D$_2$O) δ: 1.23 (d, 3H, J=7.1 Hz, β-methyl), 1.30 (d, 3H, J=6.4 Hz, CH$_3$CHOH), 1.89–2.07 (m, 5H), 2.64, 2.75 (m, 2H), 2.92–2.97 (m, 1H), 3.37–3.65 (m, 9H), 3.72–3.78 (m, 1H), 4.01, 4.06 (m, 1H), 4.24–4.39 (m, 2H), 4.42 (t, 1H).

Compound 10: (D$_2$O) δ: 1.23 (d, 3H, J=7.1 Hz, β-methyl), 1.31 (d, 3H, J=6.5 Hz, CH$_3$CHOH), 2.05–2.14 (m, 1H), 2.87–2.98 (m, 1H), 3.34–3.53 (m, 5H), 3.71–3.86 (m, 3H), 4.01–4.05 (m, 1H), 4.25–4.30 (m, 2H), 4.43 (t, 1H).

Compound 11: (D$_2$O) δ: 1.23 (d, 3H, J=7.2 Hz, β-methyl), 1.31 (d, 3H, J=6.5 Hz, CH$_3$CHOH), 2.08–2.15 (m, 1H), 2.77 (s, 3H), 2.89, 2.99 (m, 1H), 3.35–3.58 (m, 5H), 3.67–3.82 (m, 3H), 4.02–4.06 (m, 1H), 4.23–4.31 (m, 2H), 4.46 (t, 1H).

Compound 12: (D$_2$O) δ: 1.23 (d, 3H, J=7.1 Hz, β-methyl), 1.31 (d, 3H, J=6.4 Hz, CH$_3$CHOH), 2.05–2.14 (m, 1H), 2.87–2.98 (m, 1H), 3.34–3.53 (m, 5H), 3.71–3.86 (m, 5H), 3.98–4.05 (m, 1H), 4.25, 4.31 (m, 2H), 4.48 (t, 1H), 5.19–5.38 (m, 2H), 5.81–5.98 (m, 1H).

Compound 13: (D$_2$O) δ: 1.26 (d, 3H, J=7.1 Hz, β-methyl), 1.35 (d, 3H, J=6.4 Hz, CH$_3$CHOH), 2.16–2.20 (m, 1H), 2.91–3.05 (m, 1H), 3.29 (t, 2H), 3.31–3.54 (m, 5H), 3.71–3.87 (m, 5H), 4.07–4.12 (m, 1H), 4.28, 4.33 (m, 2H), 4.54 (t, 1H).

Compound 14: (D$_2$O) δ: 1.22 (d, 3H, J=7.1 Hz, β-methyl), 1.33 (d, 3H, J=6.2 Hz, CH$_3$CHOH), 2.06–2.21 (m, 1H), 2.89 (s, 3H), 3.01, 3.08 (m, 1H), 3.32–3.55 (m, 7H), 3.63–3.91 (m, 5H), 4.05–4.11 (m, 1H), 4.21–4.34 (m, 2H), 4.53 (t, 1H).

Compound 15: (D$_2$O) δ: 1.23 (d, 3H, J=7.1 Hz, β-methyl), 1.33 (d, 3H, J=6.4 Hz, CH$_3$CHOH), 2.00–2.09 (m, 4H), 2.12–2.16 (m, 1H), 2.90–2.98 (m, 1H), 3.35–3.51 (m, 9H), 3.67–3.87 (m, 3H), 4.03–4.07 (m, 1H), 4.24–4.30 (m, 2H), 4.46 (t, 1H).

Compound 16: ($D_2O$) δ: 1.16 (d, 3H, J=7.1 Hz, β-methyl), 1.21 (d, 3H, J=6.2 Hz, $CH_3CHOH$), 2.06–2.15 (m, 1H), 2.88, 2.98 (m, 1H), 3.29–3.53 (m, 9H), 3.71–3.86 (m, 7H), 3.98–4.05 (m, 1H), 4.23–4.30 (m, 2H), 4.43 (t, 1H).

EXAMPLE 16

Antibacterial Activity Test

Gram-positive Streptococcus and Staphylococcus and Gram-negative *Escherichia coli*, Pseudomonas, Salmonella, Klebsiella and Enterobacter were selected for the test. After the cells were diluted and cultured in agar, the compounds of the present invention were treated to obtain the minimum inhibitory concentration in the units of μg/ml. The results were tabulated in Table 3.

commercially available carbapenem antibiotic when administered through subcutaneously injection to the mice is shown in Table 4.

TABLE 4

|  | 10 | meropenem |
|---|---|---|
| $C_{max}$ (μg/ml) | 16.04 ± 0.96 | 7.6 ± 0.55 |
| $T_{max}$ (hr) | ≦0.33 | 0.21 ± 0.04 |
| $T_{1/2}$ (hr) | 0.32 ± 0.04 | 0.24 ± 0.22 |
| AUC (μg/ml) | 11.89 ± 1.13 | 3.29 ± 0.29 |
| AUC (hr) | 0–3 hr | 0–2 hr |

As can be seen in Table 4, the compound 10 has ca. 3 times as efficient as meropenem. This means that ⅓ of the amount of the compound 10 has the same effect as meropenem. The result of the $PD_{50}$ test using mice is tabulated in Table 5.

TABLE 3

|  |  | Minimum inhibitory concentration (μg/ml) | | | | | |
|---|---|---|---|---|---|---|---|
|  |  | 1 | 2 | 3 | 11 | 13 | 15 |
| 1 | *Streptococcus pyogenes* 308A | 0.013 | 0.013 | 0.013 | 0.013 | 0.013 | 0.013 |
| 2 | *Streptococcus pyogenes* 77A | 0.007 | 0.013 | 0.007 | 0.004 | 0.007 | 0.007 |
| 3 | *Streptococcus faecium* MD8b | 12.5 | 12.5 | 12.5 | 6.25 | 12.5 | 12.5 |
| 4 | *Staphylococcus aureus* SG511 | 0.195 | 0.391 | 0.195 | 0.098 | 0.195 | 0.195 |
| 5 | *Staphylococcus aureus* 285 | 0.195 | 0.781 | 0.391 | 0.195 | 0.195 | 0.195 |
| 6 | *Staphylococcus aureus* 503 | 0.098 | 0.195 | 0.195 | 0.098 | 0.098 | 0.195 |
| 7 | *Escherichia coli* 078 | 0.025 | 0.049 | 0.025 | 0.025 | 0.013 | 0.025 |
| 8 | *Escherichia coli* DC0 | 0.025 | 0.049 | 0.049 | 0.025 | 0.025 | 0.025 |
| 9 | *Escherichia coli* DC2 | 0.49 | 0.098 | 0.049 | 0.025 | 0.025 | 0.049 |
| 10 | *Escherichia coli* TEM | 0.025 | 0.025 | 0.025 | 0.013 | 0.013 | 0.025 |
| 11 | *Escherichia coli* 1507E | 0.025 | 0.025 | 0.025 | 0.013 | 0.025 | 0.025 |
| 12 | *Pseudomonas aeruginosa* 9027 | 0.391 | 0.781 | 1.563 | 0.391 | 1.563 | 0.391 |
| 13 | *Pseudomonas aeruginosa* 1592E | 0.391 | 0.781 | 1.563 | 0.195 | 1.563 | 0.391 |
| 14 | *Pseudomonas aeruginosa* 1771 | 0.781 | 0.781 | 1.563 | 0.195 | 1.563 | 0.781 |
| 15 | *Pseudomonas aeruginosa* 1771M | 0.391 | 0.391 | 0.391 | 0.195 | 0.391 | 0.391 |
| 16 | *Salmonella typhimurium* | 0.049 | 0.049 | 0.049 | 0.025 | 0.025 | 0.049 |
| 17 | *Klebsiella oxytoca* 1082E | 0.098 | 0.098 | 0.098 | 0.049 | 0.049 | 0.098 |
| 18 | *Klebsiella aerogenes* 1522E | 0.049 | 0.049 | 0.049 | 0.049 | 0.025 | 0.049 |
| 19 | *Enterobacter cloacae* P99 | 0.049 | 0.049 | 0.049 | 0.049 | 0.049 | 0.049 |
| 20 | *Enterobacter cloacae* 1321E | 0.025 | 0.025 | 0.025 | 0.025 | 0.013 | 0.025 |

EXAMPLE 17

Stability Against DHP-I

The stability of the compounds against the attack of a renal enzyme (DHP-I) was tested, and the results are shown in FIG. 1. In FIG. 1, ■ represents the compound 10 in Table 2, ● is the meropenem antibiotic that will be commercially available soon, and ▲ represents imipenem. In the above Figure, the horizontal and vertical axes represent time and the percent concentration of the remaining compounds, respectively. As can be seen from FIG. 1, one of the compounds, the compound 10 in Table 2 of the present invention is a little more stable than meropenem against DHP-I and markedly more stable than imipenem. In other words, the half-life of the imipenem against the enzyme was 0.5 hour, whereas that of the compound 10 of the present invention was more than 5 hours.

EXAMPLE 18

Bioavailability and $PD_{50}$ Test

The bioavailbility of the compound 10 of the present invention and the meropenem, that is the most potent

TABLE 5

| | ( ): 95% confidence interval | |
|---|---|---|
| Strains | 10 | meropenem |
| *Streptococcus* | 2.31 | 7.16 |
| *pyrogenes* A 77 | (1.36–3.94) | (4.13–12.43) |
| *Escherichia coli* 078 | 0.47 | 1.24 |
| | (0.3–0.74) | (0.74–2.08) |

*Streptococcus pyrogenes* A 77 and *Escherichia coli* 078 were selected as gram-positive and gram-negative strains, respectively. The results of $PD_{50}$ test show that the compound 10 is 3 times more efficient that meropenem. This result is consistent with the results obtained from Table 4 that the compound 10 is 3 times more potent that meropenem for the gram-positive and -negative strains. As can be seen from the Examples 16 and 17, the compounds of the present invention in Tables 1 and 2 have low minimum inhibitory concentrations for the gram-positive and -negative strains, are stable against the degradation by the renal dehydropeptidase-I and have excellent bioavailbility than meropenem.

What is claimed is:

1. Carbapenem derivatives represented by the formula I:

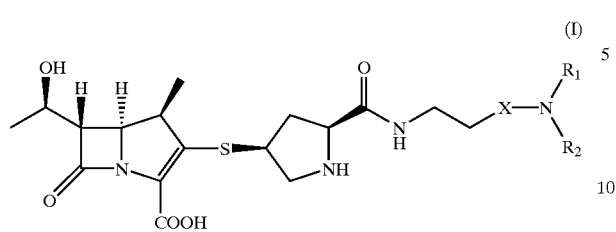
(I)

wherein, X is sulfonyl group, $R_1$ is a hydrogen or lower alkyl group, $R_2$ is a hydrogen, lower alkyl, hydroxyethyl or allyl group, and when $R_2$ is a hydroxyethyl or allyl group, $R_1$ is hydrogen or methyl; or $R_1$ and $R_2$ taken together with the nitrogen atom to which they are attached, form a heterocyclic group selected from the group consisting of pyrrolidinyl, morpholinyl and piperidinyl groups.

2. A method for preparing carbapenem derivatives represented by the formula I, said method comprising the steps of, (a) synthesizing the carbapenem intermediate of the formula VII by reacting the carbapenem nucleus represented by the formula II with diphenylchlorophosphate or trifluoromethanesulfonic anhydride in the presence of base in a reaction solvent;

(b) reacting the carbapenem intermediate represented by the formula VII with a thiol derivative represented by the formula III to produce the protected carbapenem derivative represented by the formula VIII in the presence of base in a reaction solvent; and (c) removing the protecting group from the carbapenem derivatives of the formula VIII by hydrogenation in the presence of a catalyst to produce carbapenem derivatives of the formula I

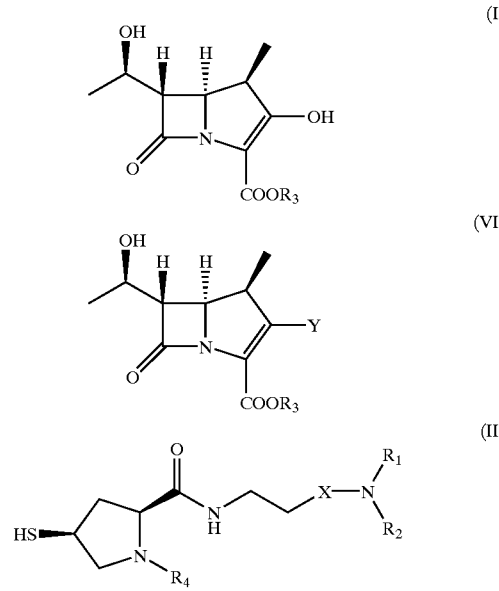

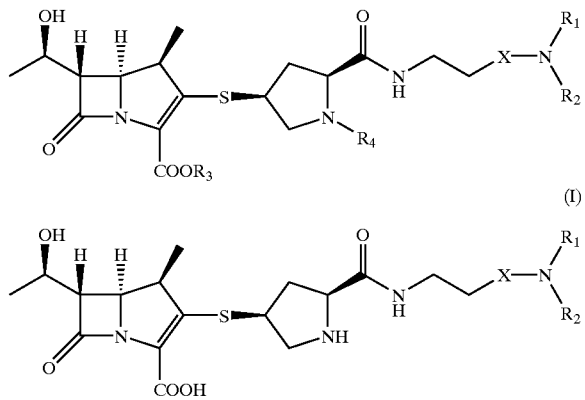

wherein, X is sulfonyl group, $R_1$ is a hydrogen or lower alkyl group and $R_2$ is a hydrogen, lower alkyl, hydroxyethyl or allyl group, and when $R_2$ is a hydroxyethyl or allyl group, $R_1$ is hydrogen or methyl; or $R_1$ and $R_2$ taken together with the nitrogen atom to which they are attached, form a heterocyclic group selected from the group consisting of pyrrolidinyl, morpholinyl and piperidinyl groups; $R_3$ is a p-nitrobenzyl or allyl protecting group; $R_4$ is a p-nitrobenzyl or allyloxycarbonyl protecting group; and Y represents $-OPO(OPh)_2$ or $-OSO_2CF_3$.

3. The method according to claim 2, wherein the solvent in the step c) is a 1:1 mixture of tetrahydrofuran and water.

4. The method according to claim 2, wherein the catalyst used in the step c) is palladium/carbon.

5. The method according to claim 2, wherein the reaction of step c) is carried out at 15~30° C. for 3 hours.

6. The method according to claim 2, wherein the hydrogenation reaction in step c) is carried out in the presence of 1~3 atm of hydrogen.

7. The carbapenem derivative of claim 1 wherein $R_1$ is hydrogen and $R_2$ is hydrogen, methyl, hydroxyethyl or allyl group.

8. The carbapenem derivative of claim 1 wherein $R_1$ is methyl and $R_2$ is a methyl, hydroxyethyl or allyl group.

9. The method of claim 2 wherein $R_1$ is hydrogen and $R_2$ is hydrogen, methyl, hydroxyethyl or allyl group.

10. The method of claim 2 wherein $R_1$ is methyl and $R_2$ is a methyl, hydroxyethyl or allyl group.

11. The method according to claim 2, wherein the base in the step a) is diisopropylamine.

12. The method according to claim 2, wherein the solvent in the step a) is acetonitrile.

13. The method according to claim 2, wherein the reaction of step a) is carried out at −5~5° C. for an hour.

14. The method according to claim 2, wherein the base used in the step b) is diisopropylamine.

15. The method according to claim 2, wherein the solvent in the step b) is acetonitrile.

16. The method according to claim 2, wherein reaction of the step b) is carried out at −5~5° C. for an hour.

* * * * *